United States Patent
Olson et al.

(10) Patent No.: US 6,645,190 B1
(45) Date of Patent: Nov. 11, 2003

(54) ABSORBENT ARTICLE WITH NON-IRRITATING REFASTENABLE SEAMS

(75) Inventors: Christopher Peter Olson, Neenah, WI (US); Lisa Ann Dimitrijevs, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/444,082

(22) Filed: Nov. 22, 1999

(51) Int. Cl.[7] .................................................. A61F 13/15
(52) U.S. Cl. ........................ 604/389; 604/386; 604/387; 604/396
(58) Field of Search ................................. 604/389, 390, 604/391, 386, 396, 385.03, 387

(56) References Cited

U.S. PATENT DOCUMENTS

| | | |
|---|---|---|
| 2,957,512 A | 10/1960 | Wade et al. |
| 3,039,466 A | 6/1962 | Wilson ........................ 128/287 |
| 3,277,547 A | 10/1966 | Billarant |
| 3,316,139 A | 4/1967 | Alford et al. |
| 3,319,307 A | 5/1967 | Marforio |
| 3,577,607 A | 5/1971 | Ikoma et al. |
| 3,694,867 A | 10/1972 | Stumpf |
| 3,842,832 A | 10/1974 | Wideman et al. |
| 3,842,837 A | 10/1974 | Sward |
| 3,943,981 A | 3/1976 | De Brabander |
| 4,051,854 A | 10/1977 | Aaron |
| 4,122,552 A | 10/1978 | Tedford ............................ 2/78 |
| 4,145,763 A | 3/1979 | Abrams et al. |
| 4,201,203 A | 5/1980 | Applegate |
| 4,205,679 A | 6/1980 | Repke et al. ................. 128/287 |
| 4,209,563 A | 6/1980 | Sisson |
| 4,244,368 A | 1/1981 | Caradonna ................... 128/287 |
| 4,253,461 A | 3/1981 | Strickland et al. ........... 128/287 |
| 4,259,957 A | 4/1981 | Sonenstein et al. |
| 4,338,938 A | 7/1982 | Seavitt |
| 4,402,690 A | 9/1983 | Redfern ........................ 604/391 |
| 4,418,123 A | 11/1983 | Bunnelle et al. |
| 4,446,189 A | 5/1984 | Romanek |
| 4,496,360 A | 1/1985 | Joffe et al. |
| 4,516,975 A | 5/1985 | Mitchell |
| 4,560,381 A | 12/1985 | Southwell .................... 604/396 |

(List continued on next page.)

FOREIGN PATENT DOCUMENTS

| | | | |
|---|---|---|---|
| CA | 2096672 | 11/1997 | ........... A61F/13/56 |
| DE | 35 33 881 A1 | 4/1986 | ........... A41B/13/04 |

(List continued on next page.)

OTHER PUBLICATIONS

Advertisement from One Step Ahead ® catalog, Late Winter 2000, cover pages and p. 26 referencing "Handy's Training Pants," and a photocopy of a package of Handy's Junior Training Pants as advertised therein.

*Primary Examiner*—Weilun Lo
*Assistant Examiner*—Jacqueline F Stephens
(74) *Attorney, Agent, or Firm*—Thomas M. Gage; H. Michael Kubicki

(57) ABSTRACT

An absorbent article includes attachment panels extending transversely outward from the absorbent assembly in one waist region and mechanical fastening components in an opposite waist region. The attachment panels cover the side hips of the wearer and define inner attachment surfaces that are adapted to refastenably engage the fastening components to maintain the absorbent article in a pant configuration.

3 Claims, 8 Drawing Sheets

U.S. PATENT DOCUMENTS

| | | | |
|---|---|---|---|
| 4,581,772 A | 4/1986 | Smith | |
| 4,585,447 A | 4/1986 | Karami | 604/385 |
| 4,610,680 A | 9/1986 | LaFleur | 604/385 |
| 4,610,682 A | 9/1986 | Kopp | 604/385 R |
| 4,615,695 A | 10/1986 | Cooper | 604/385 A |
| 4,619,649 A | 10/1986 | Roberts | 604/396 |
| 4,623,339 A | 11/1986 | Ciraldo et al. | |
| 4,650,483 A | 3/1987 | Joffe | 604/390 |
| 4,655,760 A | 4/1987 | Morman et al. | |
| 4,657,802 A | 4/1987 | Morman | |
| 4,662,875 A | 5/1987 | Hirotsu et al. | |
| 4,663,220 A | 5/1987 | Wisneski et al. | 428/221 |
| 4,699,622 A | 10/1987 | Toussant et al. | 604/389 |
| 4,701,170 A | 10/1987 | Wilson et al. | |
| 4,701,176 A | 10/1987 | Wilson et al. | |
| 4,704,116 A | 11/1987 | Enloe | |
| 4,705,710 A | 11/1987 | Matsuda | |
| 4,714,096 A | 12/1987 | Guay | |
| 4,718,901 A | 1/1988 | Singheimer | |
| 4,720,415 A | 1/1988 | Vander Wielen et al. | |
| 4,725,473 A | 2/1988 | Van Gompel et al. | |
| 4,743,239 A | 5/1988 | Cole | |
| 4,756,709 A | 7/1988 | Stevens | |
| 4,761,318 A | 8/1988 | Ott et al. | |
| 4,770,656 A | 9/1988 | Proxmire et al. | |
| 4,771,483 A | 9/1988 | Hooreman et al. | 2/237 |
| 4,789,699 A | 12/1988 | Kieffer et al. | |
| 4,834,742 A | 5/1989 | Wilson et al. | 604/389 |
| 4,847,134 A | 7/1989 | Fahrenkrug et al. | |
| 4,850,988 A | 7/1989 | Aledo et al. | 604/385.1 |
| 4,850,992 A | 7/1989 | Amaral et al. | |
| 4,863,785 A | 9/1989 | Berman et al. | |
| 4,894,060 A | 1/1990 | Nestegard | |
| 4,895,569 A | 1/1990 | Wilson et al. | |
| 4,923,456 A | 5/1990 | Proxmire | |
| 4,936,840 A | 6/1990 | Proxmire | |
| 4,938,757 A | 7/1990 | Van Gompel et al. | 604/396 |
| 4,940,464 A | 7/1990 | Van Gompel et al. | 604/396 |
| 4,963,140 A | 10/1990 | Robertson et al. | 604/389 |
| 5,019,073 A | 5/1991 | Roessler et al. | |
| 5,032,122 A | 7/1991 | Noel et al. | |
| 5,046,272 A | 9/1991 | Vogt et al. | 38/143 |
| 5,062,839 A | 11/1991 | Anderson | 604/385.1 |
| 5,087,253 A * | 2/1992 | Cooper | 604/385.1 |
| 5,104,116 A | 4/1992 | Pohjola | 271/185 |
| 5,114,781 A | 5/1992 | Morman | |
| 5,116,662 A | 5/1992 | Morman | |
| 5,151,092 A * | 9/1992 | Buell et al. | 604/385.2 |
| 5,176,671 A | 1/1993 | Roessler et al. | |
| 5,185,052 A | 2/1993 | Chappell et al. | |
| 5,224,405 A | 7/1993 | Pohjola | 83/24 |
| 5,226,992 A | 7/1993 | Morman | 156/62.4 |
| 5,242,436 A | 9/1993 | Weil et al. | 604/385.2 |
| 5,256,231 A | 10/1993 | Gorman et al. | |
| 5,315,716 A | 5/1994 | Baum | 2/227 |
| 5,318,555 A | 6/1994 | Siebers et al. | |
| 5,326,612 A | 7/1994 | Goulait | |
| 5,342,341 A | 8/1994 | Igaue et al. | 604/385.2 |
| 5,370,634 A | 12/1994 | Ando et al. | 604/385.1 |
| 5,380,313 A | 1/1995 | Goulait et al. | |
| 5,383,872 A | 1/1995 | Roessler et al. | |
| 5,385,775 A | 1/1995 | Wright | |
| 5,399,219 A | 3/1995 | Roessler et al. | 156/259 |
| 5,401,275 A | 3/1995 | Flug et al. | 604/391 |
| 5,407,439 A | 4/1995 | Goulait | |
| 5,413,654 A | 5/1995 | Igaue et al. | 156/161 |
| 5,451,219 A | 9/1995 | Suzuki et al. | |
| 5,476,702 A | 12/1995 | Datta et al. | 428/99 |
| 5,496,298 A | 3/1996 | Kuepper et al. | 604/389 |
| 5,503,908 A | 4/1996 | Faass | |
| 5,527,302 A | 6/1996 | Endres et al. | |
| 5,531,731 A | 7/1996 | Brusky | |
| 5,531,732 A | 7/1996 | Wood | 604/391 |
| 5,542,942 A | 8/1996 | Kline et al. | |
| 5,546,608 A | 8/1996 | Russano | 2/408 |
| 5,547,531 A | 8/1996 | Allen et al. | |
| 5,549,591 A | 8/1996 | Landvogt | 604/389 |
| 5,554,239 A | 9/1996 | Datta et al. | 156/66 |
| 5,569,233 A | 10/1996 | Goulait | |
| 5,591,155 A | 1/1997 | Nishikawa et al. | 604/393 |
| 5,595,567 A | 1/1997 | King et al. | |
| 5,603,708 A | 2/1997 | Seth | 604/389 |
| 5,605,735 A | 2/1997 | Zehner et al. | |
| 5,606,781 A | 3/1997 | Provost et al. | 24/452 |
| 5,611,791 A | 3/1997 | Gorman et al. | |
| 5,615,460 A | 4/1997 | Weirich et al. | |
| 5,616,394 A | 4/1997 | Gorman et al. | |
| 5,620,432 A | 4/1997 | Goulait et al. | 604/390 |
| 5,624,427 A | 4/1997 | Bergman et al. | |
| 5,624,429 A | 4/1997 | Long et al. | 604/391 |
| 5,643,397 A | 7/1997 | Gorman et al. | |
| 5,647,864 A | 7/1997 | Allen et al. | |
| H1674 H * | 8/1997 | Ames et al. | 604/389 |
| 5,655,843 A | 8/1997 | Conrad et al. | |
| 5,669,897 A | 9/1997 | Lavon et al. | 604/385.2 |
| 5,669,900 A | 9/1997 | Bullwinkel et al. | |
| 5,681,302 A | 10/1997 | Melbye et al. | |
| 5,685,873 A | 11/1997 | Bruemmer | 604/385.2 |
| 5,722,969 A | 3/1998 | Ito et al. | 604/390 |
| 5,735,840 A | 4/1998 | Kline et al. | |
| 5,749,866 A | 5/1998 | Roe et al. | 604/385.2 |
| 5,759,181 A | 6/1998 | Sayama et al. | 604/391 |
| 5,766,389 A | 6/1998 | Brandon et al. | 156/64 |
| 5,779,831 A | 7/1998 | Schmitz | |
| 5,782,819 A | 7/1998 | Tanzer et al. | |
| 5,785,699 A | 7/1998 | Schmitz | |
| 5,795,350 A | 8/1998 | Schmitz | |
| 5,814,178 A | 9/1998 | Jacobs | |
| 5,830,206 A | 11/1998 | Larsson | 604/390 |
| 5,830,298 A | 11/1998 | Jackson | |
| 5,843,068 A | 12/1998 | Allen et al. | 604/385.2 |
| 5,846,262 A * | 12/1998 | Sayama et al. | 604/391 |
| 5,851,205 A | 12/1998 | Hisada et al. | 604/390 |
| 5,853,405 A | 12/1998 | Suprise | 604/391 |
| 5,855,574 A | 1/1999 | Kling et al. | 604/392 |
| 5,876,394 A | 3/1999 | Rosch et al. | |
| 5,879,500 A | 3/1999 | Herrin et al. | 156/204 |
| 5,888,607 A | 3/1999 | Seth et al. | |
| 5,891,122 A | 4/1999 | Coates | |
| 5,891,547 A | 4/1999 | Lawless | |
| 5,897,545 A | 4/1999 | Kline et al. | 604/386 |
| 5,897,546 A | 4/1999 | Kido et al. | 604/391 |
| 5,897,547 A | 4/1999 | Schmitz | |
| 5,899,895 A | 5/1999 | Robles et al. | 604/385.2 |
| 5,906,008 A | 5/1999 | Heki et al. | 2/400 |
| 5,911,713 A | 6/1999 | Yamada et al. | 604/385.2 |
| 5,921,977 A | 7/1999 | Schmitz | |
| 5,925,027 A | 7/1999 | Schmitz | |
| 5,926,926 A | 7/1999 | Kato | 24/442 |
| 5,928,212 A | 7/1999 | Kline et al. | |
| 5,957,908 A | 9/1999 | Kline et al. | |
| 5,967,665 A | 10/1999 | MacDonald et al. | |
| 5,968,031 A | 10/1999 | Schmitz | |
| 5,997,521 A * | 12/1999 | Robles et al. | 604/385.2 |
| 5,997,981 A | 12/1999 | McCormack et al. | |
| 6,009,558 A | 1/2000 | Rosch et al. | |
| 6,022,430 A | 2/2000 | Blenke et al. | 156/73.1 |
| 6,027,485 A | 2/2000 | Matsushita et al. | |
| 6,030,373 A | 2/2000 | VanGompel et al. | 604/386 |
| 6,063,466 A | 5/2000 | Tuschy et al. | 428/40.1 |
| 6,086,571 A | 7/2000 | Guevara et al. | |

| | | | |
|---|---|---|---|
| 6,099,516 A | 8/2000 | Pozniak et al. ............. 604/386 | |
| 6,113,717 A | 9/2000 | Vogt et al. | |
| 6,115,847 A | 9/2000 | Rosch et al. | |
| 6,146,738 A | 11/2000 | Tsuji et al. | |
| D437,932 S | 2/2001 | Ruman et al. | |
| D437,933 S | 2/2001 | Fletcher et al. | |
| 6,192,521 B1 | 2/2001 | Alberts et al. | |
| D438,614 S | 3/2001 | Ratliff et al. | |
| D439,662 S | 3/2001 | Ratliff et al. | |
| 6,210,388 B1 | 4/2001 | Widlund et al. | |
| 6,213,991 B1 | 4/2001 | Kling et al. | |
| 6,230,374 B1 | 5/2001 | Widlund | |
| 6,264,643 B1 | 7/2001 | Toyoda | |
| 6,287,287 B1 | 9/2001 | Elsberg | |
| 6,302,871 B1 | 10/2001 | Nakao et al. | |
| 6,328,725 B2 | 12/2001 | Fernfors | |
| 6,329,016 B1 | 12/2001 | Shepard et al. | |
| 6,332,250 B1 | 12/2001 | Igaue et al. | |
| 6,352,528 B1 | 3/2002 | Weber et al. | |
| 6,447,497 B1 | 9/2002 | Olson | |
| 6,454,751 B1 | 9/2002 | Olson | |
| 6,461,344 B1 | 10/2002 | Widlund et al. | |
| 2002/0095131 A1 | 7/2002 | Olson | |
| 2002/0099353 A1 | 7/2002 | Olson | |
| 2003/0060794 A1 | 3/2003 | Olson | |

FOREIGN PATENT DOCUMENTS

| | | | | |
|---|---|---|---|---|
| DE | 196 54 052 C1 | 12/1997 | ........... A61F/13/58 |
| DE | 197 27 916 A1 | 6/1998 | ........... A61F/13/58 |
| EP | 0 217 032 B1 | 2/1992 | ........... A61F/13/15 |
| EP | 0 520 087 A1 | 12/1992 | ........... A61F/13/58 |
| EP | 0 526 868 A2 | 2/1993 | |
| EP | 0 321 232 B1 | 5/1993 | ........... A61F/13/15 |
| EP | 0 320 991 B1 | 5/1994 | |
| EP | 0 476 992 B1 | 7/1995 | ........... A61F/13/62 |
| EP | 0 487 921 B1 | 9/1995 | |
| EP | 0 433 951 B1 | 8/1996 | ........... A61F/13/15 |
| EP | 0 696 911 B1 | 1/1997 | ........... A61F/13/66 |
| EP | 0 756 855 A1 | 2/1997 | |
| EP | 0 570 980 B1 | 7/1997 | ........... A61F/13/15 |
| EP | 0 812 584 A2 | 12/1997 | |
| EP | 0 878 180 A2 | 11/1998 | ........... A61F/13/15 |
| EP | 0 757 550 B1 | 12/1998 | ........... A61F/13/15 |
| EP | 0 945 110 A2 | 9/1999 | |
| EP | 0 641 552 B1 | 12/1999 | ........... A61F/13/15 |
| EP | 0 755 239 B1 | 12/1999 | |
| EP | 0 800 379 B1 | 12/1999 | |
| EP | 0 719 534 B1 | 4/2000 | ........... A61F/13/58 |
| EP | 0 721 769 B1 | 5/2000 | |
| EP | 0 721 770 B1 | 5/2000 | |
| EP | 0 547 497 B2 | 7/2000 | |
| EP | 0 765 148 B1 | 11/2000 | |
| EP | 0 951 266 B1 | 3/2002 | |
| EP | 0 994 689 B1 | 9/2002 | |
| FR | 1375254 | 9/1963 | |
| GB | 1 520 740 | 8/1978 | ........... A41B/13/02 |
| GB | 2 267 024 A | 11/1993 | ........ A61F/13/166 |
| GB | 2 303 045 A | 2/1997 | ........... A61F/13/15 |
| GB | 2 315 402 A | 2/1998 | ........... A61F/13/15 |
| JP | 5-84322 U | 11/1993 | ........... A61F/13/18 |
| JP | 6-30962 A | 2/1994 | ........... A41B/13/02 |
| JP | 6-55623 U | 8/1994 | |
| JP | 6-285113 A | 10/1994 | ........... A41B/13/02 |
| JP | 7-116191 A | 5/1995 | ........... A41B/13/02 |
| JP | 9-66071 A | 3/1997 | ............. A61F/5/44 |
| JP | 9-187477 A | 7/1997 | ............. A61F/5/44 |
| JP | 11-99178 A | 4/1999 | ........... A41B/13/02 |
| WO | WO 93/17648 A1 | 9/1993 | ........... A61F/13/15 |
| WO | WO 95/02383 A1 | 1/1995 | ........... A61F/13/15 |
| WO | WO 95/18589 A1 | 7/1995 | |
| WO | WO 95/27460 A1 | 10/1995 | ........... A61F/13/15 |
| WO | WO 95/27461 A1 | 10/1995 | ........... A61F/13/15 |
| WO | WO 95/27462 A1 | 10/1995 | ........... A61F/13/15 |
| WO | WO 95/27463 A1 | 10/1995 | ........... A61F/13/15 |
| WO | WO 95/29657 A1 | 11/1995 | ........... A61F/13/15 |
| WO | WO 96/19960 A1 | 7/1996 | ........... A61F/13/15 |
| WO | WO 96/41604 A1 | 12/1996 | ........... A61F/13/15 |
| WO | WO 97/04729 A1 | 2/1997 | ........... A61F/13/15 |
| WO | WO 97/23180 A1 | 7/1997 | ........... A61F/13/15 |
| WO | WO 97/36566 A1 | 10/1997 | ........... A61F/13/15 |
| WO | WO 97/46197 A1 | 12/1997 | ........... A61F/13/56 |
| WO | WO 97/48359 A1 | 12/1997 | ........... A61F/13/15 |
| WO | WO 98/18421 A1 | 5/1998 | ........... A61F/13/15 |
| WO | WO 98/18422 A1 | 5/1998 | ........... A61F/13/62 |
| WO | WO 99/53881 A1 | 10/1999 | ........... A61F/13/62 |
| WO | WO 99/65441 A1 | 12/1999 | |
| WO | WO 00/15069 A1 | 3/2000 | |
| WO | WO 00/19950 A1 | 4/2000 | |
| WO | WO 00/19951 A1 | 4/2000 | |
| WO | WO 00/20206 A1 | 4/2000 | |
| WO | WO 00/20207 A1 | 4/2000 | |
| WO | WO 00/23025 A1 | 4/2000 | |
| WO | WO 00/27236 A1 | 5/2000 | |
| WO | WO 00/27328 A1 | 5/2000 | |
| WO | WO 00/27329 A1 | 5/2000 | |
| WO | WO 00/30581 A1 | 6/2000 | |
| WO | WO 00/30584 A1 | 6/2000 | |
| WO | WO 00/35395 A2 | 6/2000 | |
| WO | WO 00/35396 A1 | 6/2000 | |
| WO | WO 00/35397 A1 | 6/2000 | |
| WO | WO 00/35399 A1 | 6/2000 | |
| WO | WO 00/37009 A2 | 6/2000 | |
| WO | WO 00/37016 A1 | 6/2000 | |
| WO | WO 00/74621 A1 | 12/2000 | |
| WO | WO 01/88245 A2 | 11/2001 | |

\* cited by examiner

ABSORBENT ARTICLE WITH NON-IRRITATING REFASTENABLE SEAMS

BACKGROUND OF THE INVENTION

The present invention relates to absorbent articles which are adapted to contain body exudates. More particularly, the invention pertains to pant-like disposable absorbent articles having non-irritating refastenable mechanical seams, and methods of making such disposable absorbent articles.

Current disposable absorbent training pants for children going through the potty training stage have proved to be a particularly desirable and useful product. Such training pants generally include an absorbent chassis including a liquid impervious outer cover, a liquid pervious bodyside liner and an absorbent structure. The training pants further include elastic side panels that are permanently bonded to opposite side edges of the absorbent chassis. The chassis and side panels thereby form a unitary waist opening and two leg openings. The fit of the pants may be further enhanced by gathering means along the waist and leg openings.

The components of traditional training pants are permanently seamed together to provide a pant product. These products are particularly appealing to caregivers and are useful in the toilet training process because the pant has a very garment-like look. Children identify diaper products with babies, and most children do not like being identified with or as babies. Consequently, these children do not want to wear baby diapers, and instead prefer to wear training pants that look like adult underwear. Thus, the switch from a traditional diaper to a more garment-like or underwear-like training pant can be an important step in the toilet training process.

One drawback with current training pants, however, is that the manner of applying them is limited to being pulled on like a pant. Applying the product like a pant is advantageous in many instances, and is particularly suited for active, walking children. Even for the same child, however, there may be times when it would be useful to apply the product like a diaper. For instance, it might be more convenient to apply the product like a diaper when there is a desire not to remove the child's shoes. Because it is difficult to know when a particular mode of applying the garment will be needed, it is beneficial to have a garment that is adaptable to being used either as a diaper or as a pant. This is preferable to keeping both types of garments available. A product that can be applied either like a diaper or a pant permits the interior of the product to be easily checked without having to pull the product downward.

Thus, it would be desirable to have a disposable absorbent article that provides the garment-like look of a traditional training pant, includes fastening components to allow application like either a diaper or a pant, and of course minimizes the likelihood of the fastening components coming into contact with the skin of the wearer.

SUMMARY OF THE INVENTION

In response to the above-referenced unfulfilled need in the art, a new pant-like disposable absorbent article and a method of making such a disposable absorbent article have been discovered. The absorbent article includes a fastening system that can be repeatedly fastened, unfastened and refastened. The fastening system includes at least one fastening component disposed in one waist region and a pair of side attachment panels disposed in the other waist region that are adapted to releasably engage the at least one fastening component. The use of the side attachment panels to engage the fastening component reduces the chance for skin irritation because potentially irritating fastener components, such as hook fasteners, are disposed on the exterior surface of one waist region and covered by the side attachment panels.

The fastening components and the attachment panels form refastenable seams for securing the first and second waist regions together. The refastenable seams allow the product to be either pulled on like a pant or applied like a diaper. If the training pant becomes soiled during use, the attachment panels can be disengaged from the fastening components to easily remove the training pant from the waist of the wearer with reduced risk of undesirably soiling the clothes or legs of the wearer. Further, the attachment panels can also be easily disengaged to inspect the training pant for possible soiling. Thus, the training pant is configured to be pulled on or off over the hips of the wearer such as conventional training pants and can be readily applied or removed by disengaging the fastening system similar to conventional diapers. Moreover, the attachment panels can be repositioned if necessary after the training pant has been pulled on over the legs and hips of the wearer.

Hence, in one embodiment, the present invention relates to an absorbent article defining a longitudinal axis, an overall length dimension measured parallel to the longitudinal axis, a transverse axis, first and second longitudinally spaced waist regions, a crotch region which extends between and interconnects the first and second waist regions, an inner surface and an opposite outer surface. The absorbent article is adapted to provide a pant configuration having a waist opening and a pair of leg openings. The absorbent article includes an absorbent chassis comprising an absorbent assembly, and attachment panels extending transversely outward from the absorbent assembly in the first waist region. The attachment panels have a length dimension that is about 20 percent or greater of the overall length dimension, and each attachment panel includes a nonwoven substrate that extends from the waist opening to one of the leg openings and defines an inner attachment surface. At least one fastening component is disposed in the second waist region on the outer surface, and the at least one fastening component includes a mechanical fastening element that is adapted to refastenably engage the inner attachment surfaces. The refastenable engagement of the mechanical fastening element and the inner attachment surfaces maintains the absorbent article in the pant configuration.

In particular embodiments, each side attachment panel is elastomeric in a direction parallel to the transverse axis from the waist end edge to the leg end edge to provide automatic fit of the product around the wearer. The attachment panels are desirably formed of elastomeric nonwoven materials, comprising for example a nonwoven substrate and an elastomeric material. Suitable elastomeric materials may take a wide variety of forms, such as a plurality of elastomeric strands, an elastomeric film, a web of elastomeric filaments, or the like. In particular embodiments, the attachment panels consist essentially of the elastomeric nonwoven materials such that no separate fastening materials or fastening elements, loop material for example, are formed from or attached to the attachment panels. Most desirably, the attachment panels consist of an elastomeric nonwoven without any additional materials or elements. The elastomeric nonwoven suitably comprises a composite material including an elastomeric layer and an inner nonwoven layer that forms an inner attachment surface. The elastomeric layer can gather or shirr the inner nonwoven layer so that it has a corrugated and/or creped structure that is readily engageable by the fastening components. The elastomeric layer can be sandwiched between inner and outer nonwoven layers.

The refastenable seams are formed when the side attachment panels are engaged with the fastening components. The refastenable seams are desirably relatively thin, narrow and flexible to afford the look and feel of a cloth garment. Thus, in particular embodiments, the refastenable seams have a length-to-width ratio of about 2 or greater, such as about 2 to about 25, particularly about 5 or greater, such as about 5 to about 8. The refastenable seams define a length dimension and a width dimension that is perpendicular to the length dimension. For a child of about 9 to about 15 kilograms (20–34 lbs.), for example, the length dimension is desirably from about 5 to about 13 centimeters, such as about 10 centimeters, and the width dimension is desirably from about 0.5 to about 3 centimeters, such as about 2 centimeters. Desirably although not necessarily, the length dimension can be aligned generally parallel to the longitudinal axis of the absorbent article and the width dimension can be aligned generally parallel to the transverse axis of the absorbent article. The term "generally parallel" as used herein refers to an angle within about 35 degrees or less of the referenced axis, and more particularly within about 20 degrees or less of the referenced axis.

The fastening components desirably comprise mechanical fastening elements rather than adhesive fastening elements. Suitable mechanical fastening elements can be provided by interlocking geometric shaped materials, such as hooks, loops, bulbs, mushrooms, arrowheads, balls on stems, male and female mating components, buckles, snaps, or the like. In particular embodiments, the fastening components and mating fastening components comprise hook-and-loop fastening elements. One skilled in the art will recognize that the shape, density and polymer composition of the hooks and loops may be selected to obtain the desired level of securement between the fastening components and the mating fastening components. A more aggressive hook material may comprise a material with a greater average hook height, a greater percentage of directionally-aligned hooks, or a more aggressive hook shape.

Hence, in another embodiment, the present invention relates to an absorbent article defining a longitudinal axis, a transverse axis, front and back longitudinally spaced waist regions, a crotch region which extends between and interconnects the front and back waist regions, an inner surface and an opposite outer surface. The absorbent article is adapted to provide a pant configuration having a waist opening and a pair of leg openings. An absorbent chassis of the absorbent article includes a liquid permeable bodyside liner, a liquid impermeable outer cover bonded to the bodyside liner, and an absorbent assembly disposed between the bodyside liner and the outer cover. First and second attachment panels are bonded to the absorbent chassis in the back waist region. The attachment panels extend transversely outward from the absorbent chassis and consist essentially of an elastomeric nonwoven material defining an inner attachment surface. The absorbent article also includes at least one fastening component disposed in the front waist region on the outer surface. The at least one fastening component includes a plurality of engaging elements that project outward from the outer surface and are adapted to refastenably engage the attachment surfaces of the attachment panels. The refastenable engagement of the attachment panels to the at least one fastening component maintains the absorbent article in the pant configuration.

Hence, in a further embodiment, the present invention relates to an absorbent article including an absorbent chassis. First and second attachment panels extending transversely outward from the absorbent assembly in the back waist region. The attachment panels consist essentially of an elastomeric nonwoven material and define inner attachment surfaces. At least one fastening component is disposed in the front waist region on the outer surface. The at least one fastening component includes a plurality of engaging elements that project outward from the outer surface and are adapted to refastenably engage the attachment surfaces of the attachment panels. The refastenable engagement of the attachment panels to the at least one fastening component maintains the absorbent article in the pant configuration.

As disclosed in copending U.S. patent application Ser. No. 60/112,709, filed on Dec. 18, 1998 by C. P. Olson et al. and titled "Absorbent Articles Having Differential Strength Refastenable Seam," the refastenable seam may include one or more main refastenable attachment zones and one or more enhanced refastenable attachment zones. The main and enhanced refastenable attachment zones may be constructed to provide differential levels of securement, and particularly augmented levels of securement at locations which are subject to greater levels of separation forces.

As disclosed in copending U.S. patent application Ser. No. 60/112,775, filed on Dec. 18, 1998 by C. P. Olson and titled "Absorbent Articles Having Hinged Fasteners," the refastenable seam may comprise individual fastening materials with narrow spacings therebetween. The narrow spacings provide a desirable hinge to improve fit and securement of the fastening components.

The disclosed absorbent articles are adapted to be worn adjacent to the body of a wearer to absorb and contain various exudates discharged from the body. The absorbent articles are desirably pre-fastened to provide a pant-like product for the user. The product can then be pulled on like a conventional training pant, and subsequently checked or removed with the ease of a diaper-like product. Moreover, the product may be applied like a diaper rather than like a pant. Supplemental releasable fastening means such as frangible point bonds may be employed to maintain the absorbent article in a pant configuration until the user intentionally disengages the fasteners.

The fastening system allows for easy inspection of the interior of the pant-like product. If necessary, the fastening system also allows the pant to be removed quickly and easily. This is particularly beneficial when the pant contains messy excrement. If desired, the caregiver can completely remove the pant-like product and replace it with a new one without having to remove the child's shoes and clothing. The present fastening system may be used with a wide variety of absorbent products, including training pants, diapers, incontinence garments, or other garments using mechanical or adhesive fasteners.

A more detailed description of the construction and design of one form of training pant can be found in U.S. Pat. No. 4,940,464 issued Jul. 10, 1990 to Van Gompel et al., which is incorporated herein by reference. The Van Gompel et al. patent describes various materials of which the training pant can be made, and a method of constructing a training pant. In general, the various components of the training pant can be assembled employing various types of suitable attachment means, such as adhesive, sonic and thermal bonds or combinations thereof.

DEFINITIONS

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Flexible" refers to materials which are compliant and which will readily conform to he general shape and contours of the wearer's body.

"Force" includes a physical influence exerted by one body on another, which produces acceleration of bodies that are free to move and deformation of bodies that are not free to move. Force is expressed in grams per unit area.

"Graphic" refers to any design, pattern, or the like that is visible on an absorbent article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Integral" is used to refer to various portions of a single unitary element rather than separate structures bonded to or placed with or placed near one another.

"Inward" and "outward" refer to positions relative to the center of an absorbent article and particularly transversely and/or longitudinally closer to or away from the longitudinal and transverse center of the absorbent article.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member" when used in the singular can have the dual meaning of a single element or a plurality of elements.

"Nonwoven web" means a web of material which is formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use.

"Permanently bonded" refers to the joining, adhering, connecting, attaching, or the like, of two elements of an absorbent garment such that the elements tend to be and remain bonded during normal use conditions of the absorbent garment.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length.

Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a non-softened condition when cooled to room temperature.

These terms may be defined with additional language in the remaining portions of the specification.

BRIEF DESCRIPTION OF THE DRAWINGS

The above-mentioned and other features of the present invention and the manner of attaining them will become more apparent, and the invention itself will be better understood by reference to the following description and the accompanying drawings, wherein similar features in different figures have been given the same reference numeral.

DETAILED DESCRIPTION OF THE DRAWINGS

The principles of the present invention can be incorporated into any suitable disposable absorbent article and its method of manufacture. Examples of such suitable articles include diapers, training pants, feminine hygiene products, incontinence products, other personal care or health care garments, or the like. For ease of explanation, the description hereafter will be in terms of a child's training pant.

Figure 1:
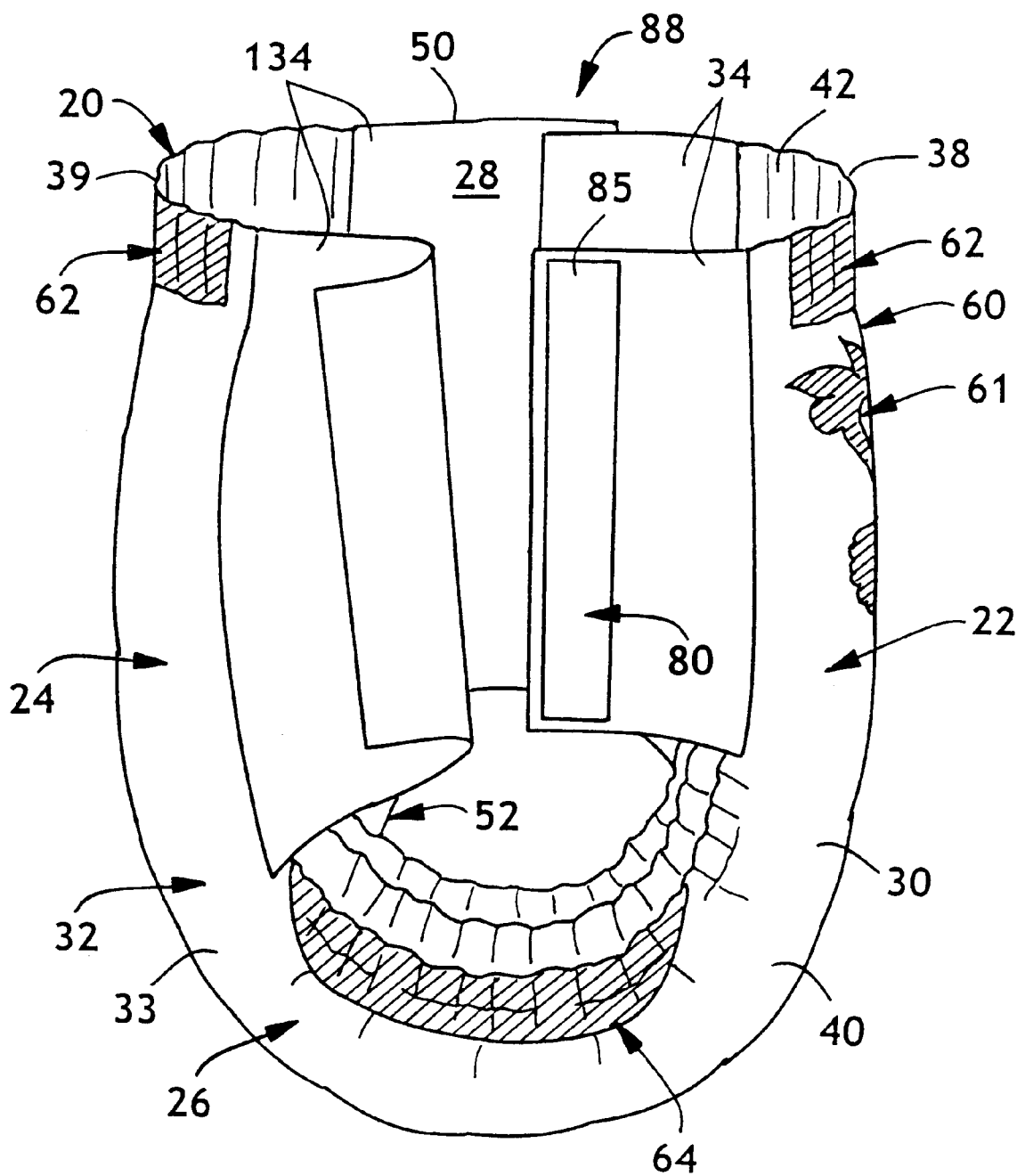
FIG. 1 illustrates a side view of one type of disposable absorbent article incorporating the principles of the present invention, where the fastening system is shown engaged on one side of the absorbent article and disengaged on the other side of the absorbent article.

With reference to FIG. 1, a disposable absorbent article, such as a training pant 20, is illustrated in a partially fastened condition. The training pant 20 comprises an absorbent chassis 32 and a fastening system 80. The absorbent chassis 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIGS. 2 and 3, the absorbent chassis 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39.

Figure 2:
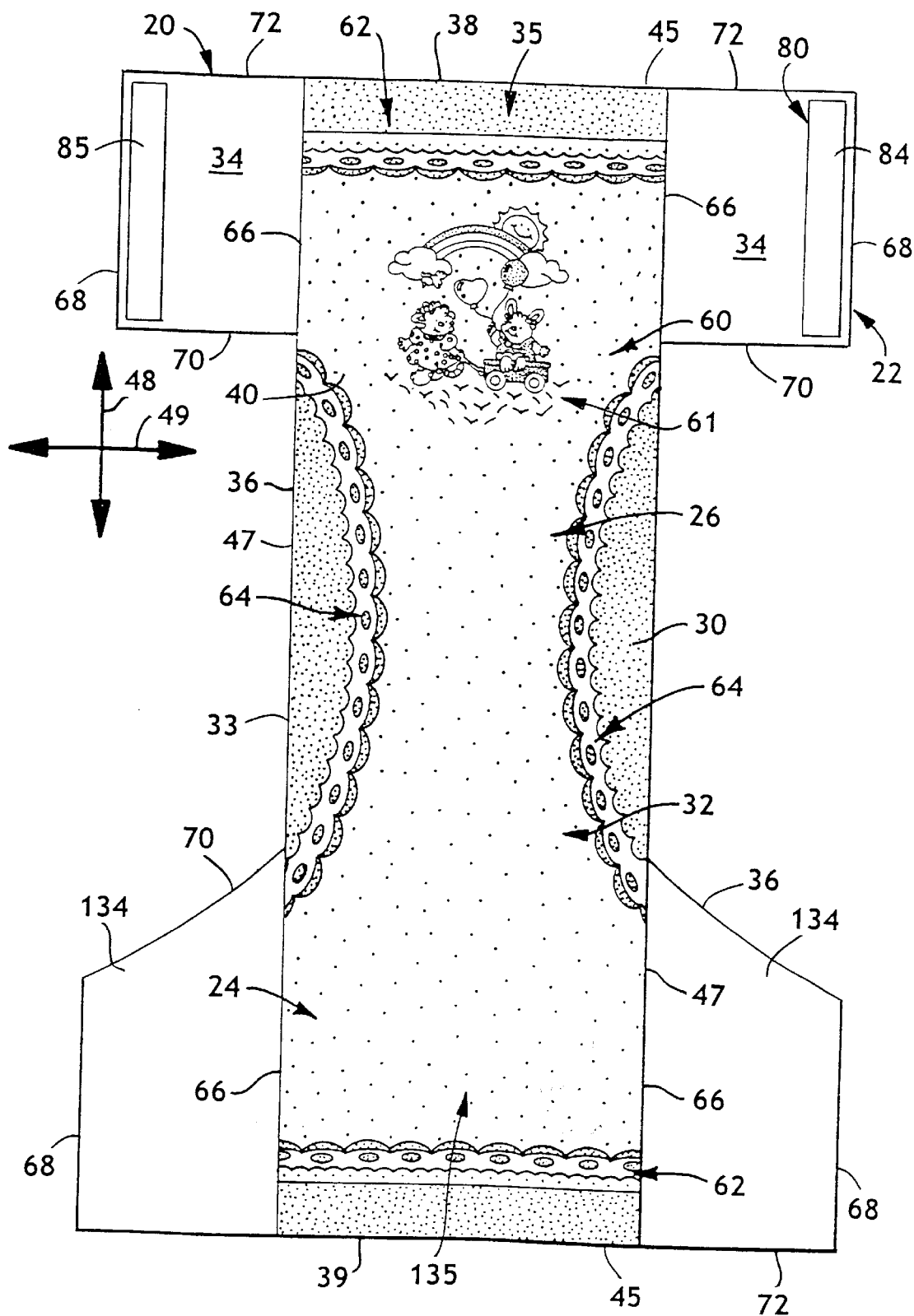
FIG. 2 illustrates a plan view of the disposable absorbent article shown in FIG. 1 in an unfastened, stretched and laid flat condition, and showing the surface of the article that faces away from the wearer.
Figure 3:
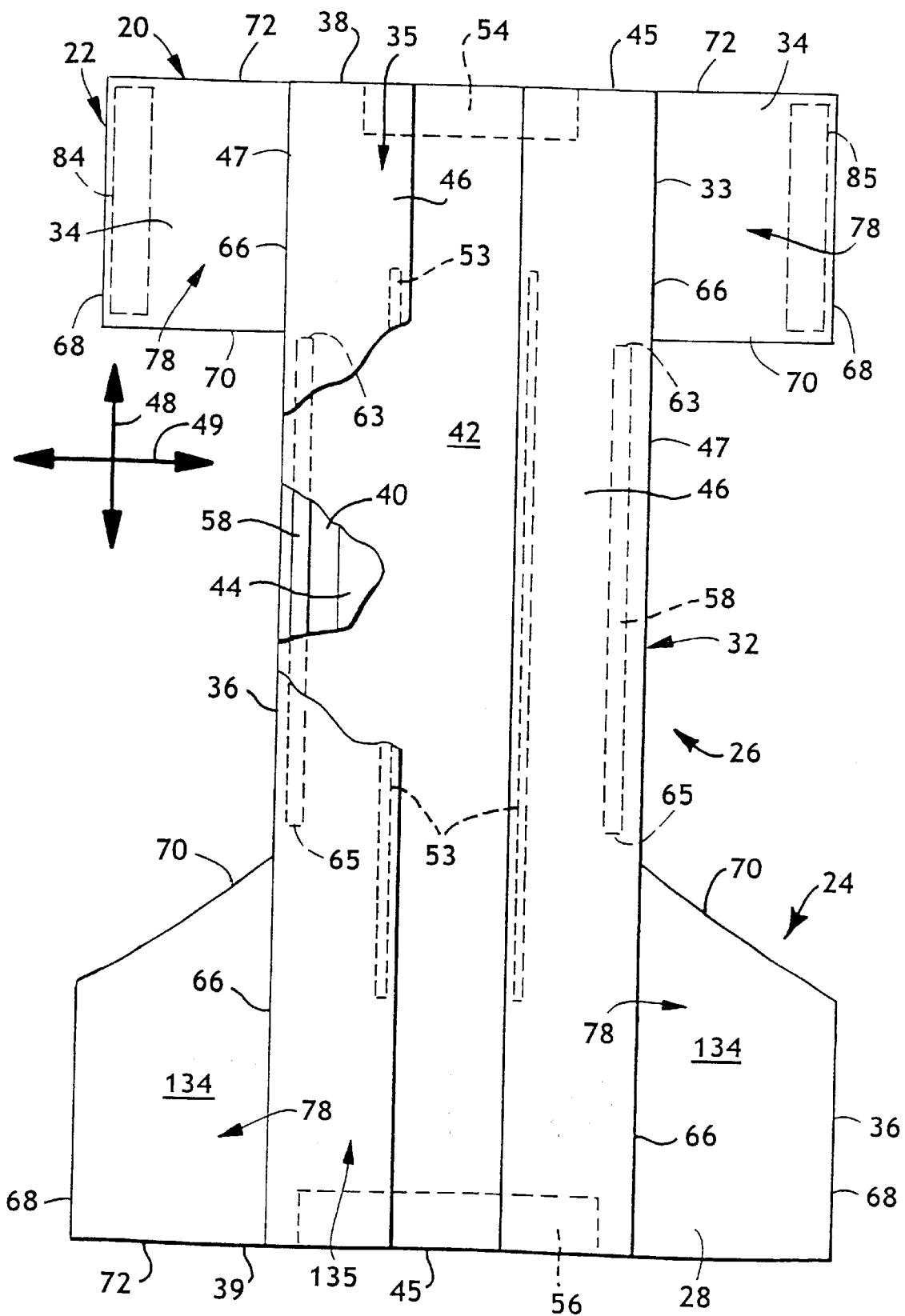
FIG. 3 illustrates a plan view similar to FIG. 2, but showing the surface of the article that faces the wearer when the article is worn, and with portions cut away to show the underlying features.

The illustrated absorbent chassis 32 comprises a rectangular composite structure 33, a pair of transversely opposed front side panels 34, and a pair of transversely opposed back side panels 134. The back side panels 134 of the illustrated embodiment will also be referred to interchangeably as "attachment panels". The composite structure 33 and side panels 34 and 134 may be integrally formed or comprise two or more separate elements, as shown in FIG. 1. The illustrated composite structure 33 comprises an outer cover 40, a bodyside liner 42 (FIGS. 1 and 3) which is connected to the outer cover in a superposed relation, an absorbent assembly 44 (FIG. 3) which is located between the outer cover and the bodyside liner, and a pair of containment flaps 46 (FIG. 3). The rectangular composite structure 33 has opposite linear end edges 45 that form portions of the front and back waist edges 38 and 39, and opposite linear side edges 47 that form portions of the side edges 36 of the absorbent chassis 32 (FIGS. 2 and 3). For reference, arrows 48 and 49 depicting the orientation of the longitudinal axis and the transverse axis, respectively, of the training pant 20 are illustrated in FIGS. 2 and 3.

With the training pant 20 in the fastened position as partially illustrated in FIG. 1, the front and back waist regions 22 and 24 are joined together to define a three dimensional pant configuration having a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The front and back side panels 34 and 134 comprise the portions of the training pant 20 which, when worn, are positioned on the hips of the wearer.

The front waist region 22 of the absorbent chassis 32 includes the transversely opposed front side panels 34 and a front center panel 35 (FIGS. 2 and 3) positioned between and connecting the side panels. The back waist region 24 of the absorbent chassis 32 includes the transversely opposed back side panels 134 and a back center panel 135 (FIGS. 2 and 3) positioned between and connecting the side panels. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52.

The absorbent chassis 32 is configured to contain and/or absorb any body exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably includes a front waist elastic member 54, a rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38 and 39, and can extend over part or all of the waist edges. The leg elastic members 58 are desirably operatively joined to the outer cover 40 and/or bodyside liner 42 along the opposite side edges 36 and positioned in the crotch region 26 of the training pant 20. The leg elastic members 58 are desirably longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 are desirably located adjacent the longitudinally innermost parts of the front side panels 34, and the back terminal points 65 are desirably located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials may be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del., U.S.A.

The outer cover 40 desirably comprises a material that is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as liquid impermeable inner layer, or a single layer liquid impermeable outer cover 40, is a 1.0 mil polyethylene film commercially available from Edison Plastics Company of South Plainfield, N.J., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn., U.S.A.

As shown in FIGS. 1 and 2, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young girls, includes a registered outer cover graphic 60. In this design, the registered graphic 60 includes simulated a primary pictorial image 61, waist ruffles 62, and simulated leg ruffles 64. The primary pictorial image 61 includes a rainbow, sun, clouds, animal characters, wagon and balloons. Any suitable design can be utilized for a training pant intended for use by young girls, so as to be aesthetically and/or functionally pleasing to them and the caregiver. The appearance-related components are desirably positioned on the training pant 20 at selected locations, which can be carried out using the methods disclosed in U.S. Pat. No. 5,766,389 issued Jun. 16, 1998 to Brandon et al., which is incorporated herein by reference. The primary pictorial image 61 is desirably positioned in the front waist region 22 along the longitudinal centerline of the training pant 20.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like.

The absorbent assembly 44 (FIG. 3) is positioned between the outer cover 40 and the bodyside liner 42, which components can be joined together by any suitable means such as adhesives as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 may suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. The fluff and superabsorbent particles may also be selectively placed into desired zones of the absorbent assembly 44 to better contain and absorb body exudates. The concentration of the superabsorbent particles may also vary through the thickness of the absorbent assembly 44. Alternatively, the absorbent assembly 44 may comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and comprises a blend of wood pulp fluff and superabsorbent material. One preferred type of fluff is identified with the trade designation CR1654, available from Kimberly-Clark Corporation, Neenah, Wis., U.S.A., and is a bleached, highly absorbent sulfate wood pulp containing primarily soft wood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that maintains the integrity and/or shape of absorbent assembly.

The absorbent chassis 32 can also incorporate other materials that are designed primarily to receive, temporarily store, and/or transport liquid along the mutually facing surface with absorbent assembly 44, thereby maximizing the absorbent capacity of absorbent assembly. One suitable material is referred to as a surge layer (not shown) and comprises a material having a basis weight of about 50 grams per square meter, and comprising a through-air-bonded-carded web of a homogenous blend of 60 percent 3 denier bicomponent fiber comprising a polyester core/polyethylene sheath, commercially available from BASF Corporation, and 40 percent 6 denier polyester fiber, commercially available from Hoechst Celanese Corporation, Portsmouth, Va. U.S.A.

As noted previously, the illustrated training pant 20 has front and back side panels 34 and 134 disposed on each side of the absorbent chassis 32. Alternatively, the training pant 20 may include side panels that extend outward from the composite structure 33 in only one of the waist regions 22 or 24 (see FIG. 9). These transversely opposed front side panels 34 and transversely opposed back side panels 134 can be permanently bonded to the composite structure 33 of the absorbent chassis 32 in the respective front and back waist regions 22 and 24, and are releasably attached to one another by the fastening system 80. More particularly, as shown best in FIGS. 2 and 3, the front side panels 34 can be permanently bonded to and extend transversely beyond the linear side edges 47 of the composite structure 33 in the front waist region 22 along attachment lines 66, and the back side panels 134 can be permanently bonded to and extend transversely beyond the linear side edges of the composite structure in the back waist region 24 along attachment lines 66. The side panels 34 and 134 can be attached using attachment means known to those skilled in the art such as adhesive, thermal or ultrasonic bonding. The side panels can alternatively be formed as a portion of a component of the composite structure 33, such as the outer cover or the bodyside liner.

The illustrated side panels 34 and 134 each define a distal edge 68 that is spaced from the attachment line 66, a leg end edge 70 disposed toward the longitudinal center of the training pant 20, and a waist end edge 72 disposed toward a longitudinal end of the training pant. The leg end edge 70 and waist end edge 72 extend from the side edges 47 of the composite structure 33 to the distal edges 68. The leg end edges 70 of the side panels 34 and 134 form part of the side edges 36 of the absorbent chassis 32. In the back waist region 24, the leg end edges 70 are desirably angled relative to the transverse axis 49 to provide greater coverage toward the back of the pant as compared to the front of the pant. The waist end edges 72 are desirably parallel to the transverse axis 49. The waist end edges 72 of the front side panels 34 form part of the front waist edge 38 of the absorbent chassis 32, and the waist end edges 72 of the back side panels 134 form part of the back waist edge 39 of the absorbent chassis.

Figure 8:
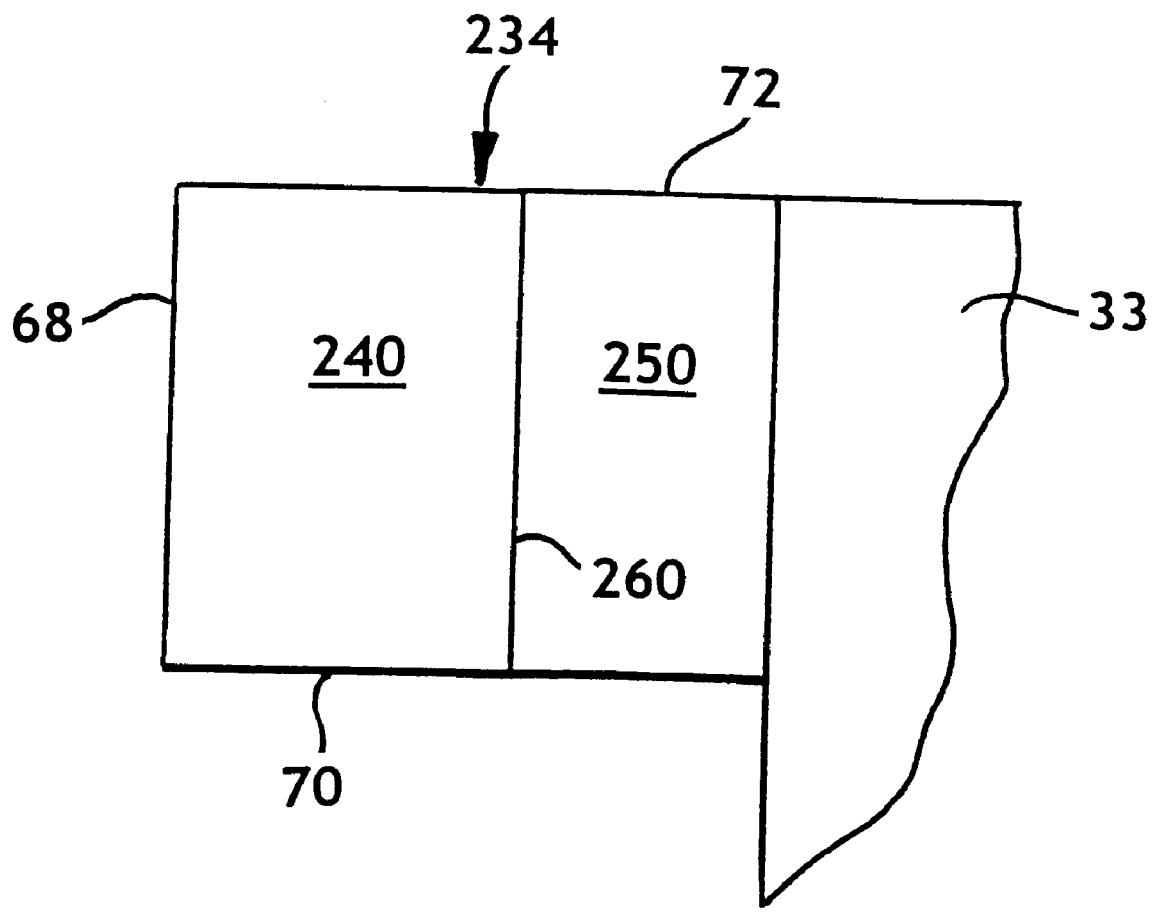
FIG. 8 illustrates a plan view of an alternative side panel configuration.

Each of the side panels 34 and 134 can include one or more individual, distinct pieces of material. In particular embodiments, for example, each side panel 34 and 134 can include first and second side panel portions that are joined at a seam, with at least one of the portions comprising an elastomeric material. By way of illustration, FIG. 8 shows an alternative side panel configuration in which a front or back side panel 234 comprises an outer member 240 and an inner member 250 that are joined at a seam 260. The seam can be formed using attachment means know to those skilled in the art such as adhesive, thermal or ultrasonic bonding. Desirably, at least one of the members 240 and 250 comprises an elastomeric material. Still alternatively, each individual side panel 34 and 134 can include a single piece of material which is folded over upon itself along an intermediate fold line (not shown).

The side panels 34 and 134 desirably comprise an elastic material capable of stretching in a direction parallel to the transverse axis 49 of the training pant 20. In particular embodiments, the front and back side panels 34 and 134 may each comprise an interior portion 78 (FIG. 3) disposed between the distal edge 68 and the respective front or back center panel 35 or 135. In the illustrated embodiment, the interior portions 78 are disposed between the distal edges 68 and the side edges 47 of the rectangular composite structure 33. The elastic material of the side panels 34 may be disposed in the interior portions 78 to render the side panels elastomeric in a direction parallel to the transverse axis 49. Most desirably, each side panel 34 is elastomeric from the waist end edge 72 to the leg end edge 70. More specifically, individual samples of side panel material, taken between the waist end edge 72 and the leg end edge 70 parallel to the transverse axis 49 and having a length from the attachment line 66 to the distal edge 68 and a width of 2 centimeters, are all elastomeric.

In particular embodiments for improved fit and appearance, the attachment panels 134 desirably have a length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the attachment panels 134 desirably have a length dimension of about 10 centimeters or greater, such as about 15 centimeters. As illustrated the attachment panels 134 extend from the waist opening 50 to one of the leg openings 52.

Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Mormon; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42.

The training pant 20 according to the present invention also includes a fastening system 80 for securing the training pant about the waist of the wearer (FIGS. 2 and 3). The illustrated fastening system 80 includes the first and second back side panels 134 that are adapted to refastenably connect to first and second fastening components 84 and 85. Because the first and second back side panels 134 form part of the fastening system, they are also referred to herein as the first and second attachment panels 134. In one embodiment, one surface of each of the first and second fastening components 84 and 85 comprises a plurality of engaging elements that project from that surface. The engaging elements of these fastening components 84 and 85 are adapted to repeatedly engage and disengage the inner surfaces 28 of the attachment panels 134, which surfaces are also referred to as inner attachment surfaces.

In one particular embodiment, the first and second fastening components 84 and 85 each comprise hook type fasteners and the inner surface 28 of the first and second attachment panels 134 include a lofty nonwoven material that is releasably engageable with the hook type fasteners. The attachment panels 134 can comprise a variety of woven and nonwoven materials having threads or fibers of suitable size and spacing so that the inner attachment surfaces engage and/or entangle the engaging elements of the first and second fastening components 84 and 85. The inner attachment surfaces 28 of the attachment panels 134 are desirably constructed of materials that are relatively soft against the wearer's skin and somewhat durable to provide more than one refastenable connection. with the fastening components. The inner attachment surfaces 28 of the attachment panels 134 can comprise, for example, a spunbond material, a knit fabric, a thermal bonded carded web, a hydroentangled web, or the like that provides several engagements with the fastening components prior to significant destruction of the attachment panel material.

Hook type fasteners typically comprise a fabric or material having a base or backing structure and a plurality of hook members extending upwardly from at least one surface of the backing structure. In contrast to the loop type fasteners which desirably comprise a flexible fabric, the hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material may be molded or extruded of nylon, polypropylene or another suitable material. Suitable single-sided hook materials for the first fastening components 82 and 83 are available from Velcro Industries B.V., Amsterdam, Netherlands or affiliates thereof, and are identified as Velcro HTH-829 with a unidirectional hook pattern and having a thickness of about 0.089 millimeters (3.5 mils) and HTH-851 with a unidirectional hook pattern and having a thickness of about 0.051 millimeters (2 mils).

With particular reference to FIG. 2, the first and second fastening components 84 and 85 are located on the outer surface 30 of the training pant 20 in the front waist region 22. The fastening components 84 and 85 are referred to as located on the outer surface 30 despite the fact that they are covered by the attachment panels 134 when the absorbent article is in a pant configuration. The first and second fastening components can be positioned along the distal edges 68 of the front side panels 34, and abutting or adjacent to the waist end edge 72. In certain embodiments, for example, the first and second fastening components 84 and 85 are located within about 2 centimeters, and more particularly within about 1 centimeter, of the distal edges 68, the waist end edges 72, and the leg end edges 70. The fastening components 84 and 85 may be adhered to the side panels 34 or the outer surface 30 by any means known to those skilled in the art such as adhesive bonds, sonic bonds or thermal bonds.

In an alternative embodiment, the training pant 20 includes only a single fastening component disposed in the front waist region 22 for refastenably connecting the first and second back side panels 134 (not shown). The first and second fastening components 84 and 85 are desirably rectangular, although they may alternatively be square, round, oval, curved or otherwise nonrectangularly shaped.

When the first and second attachment panels 134 and the fastening components 84 and 85 are releasably engaged, the absorbent article assumes a three dimensional pant configuration. In particular, the side edges 36 of the absorbent chassis 32 in the crotch region 26 define the leg openings 52, and the waist edges 38 and 39 of the absorbent chassis, including the waist end edges 72 of the side panels, define the waist opening 50.

When connected, the first and second attachment panels 134 and the fastening components 84 and 85 form a refastenable seam 88 (FIG. 1). In particular embodiments, each of the fastening components 84 and 85 defines a length dimension aligned generally parallel with the longitudinal axis 48 of the training pant 20 and a width dimension aligned generally parallel with the transverse axis 49 of the training pant. For a child of about 9 to about 15 kilograms (20–30 lbs.), for example, the length dimension of the fastening components is desirably from about 5 to about 13 centimeters, such as about 10 centimeters, and the width dimension is desirably from about 0.5 to about 3 centimeters, such as about 1 centimeter. The fastening components desirably have a length-to-width ratio of about 2 or greater, such as about 2 to about 25, and particularly about 5 or greater, such as about 5 to about 8.

The refastenable seams 88 desirably extend substantially the entire distance between the waist opening 50 and the leg openings 52 when the attachment panels 134 are engaged with the fastening components 84 and 85. More specifically, the refastenable seams 88 can cover about 80 to 100 percent, and particularly about 90 to about 98 percent, of the distance between the waist opening 50 and each leg opening 52, which distance is measured parallel to the longitudinal axis 48. To construct the seams 88 to extend substantially the entire distance between the waist and leg openings 50 and 52, the fastening components 84 and 85 can be formed to cover about 80 to 100 percent, and more particularly about 90 to about 98 percent, of the distance between the waist end edge 70 and the leg end edge 72 of the side panels 34.

The absorbent chassis 32 and the fastening system 80 together define a refastenable pant having a waist opening 50 and a pair of leg openings 52. When the fastening system is engaged, it can be appreciated that the refastenable pant includes a pair of elastomeric front side panels 34 extending from the waist opening to each leg opening, a pair of elastomeric back side panels 134 extending from the waist opening to each leg opening, a pair of refastenable seams 88 extending from the waist opening to each leg opening and positioned between the elastomeric front and back side panels, an elastomeric front waistband 54 disposed in the front waist region and positioned between the pair of elastomeric front side panels, an elastomeric back waistband 56 disposed in the back waist region and positioned between the pair of elastomeric back side panels, and a pair of elastomeric leg members 58 which partially encircle each leg opening. Each elastomeric leg member 58 extends from adjacent an elastomeric front side panel 34 in the front waist region 22 to adjacent an elastomeric back side panel 134 in the back waist region 24.

In certain aspects, the present fastening system 80 differs from conventional fastening systems in that it does not include separate patches, strips or tabs of fastening component material that engage the first and second fastening components 84 and 85. For example, many conventional fastening systems employ complementary patches, strips or tabs of fastening material, such as hook and loop materials, to form a refastenable connection between the front and back waist regions 22 and 24.

In contrast, the present fastening system 80 utilizes the side panels to refastenably connect to the first and second fastening components 84 and 85. In particular embodiments, the inner attachment surfaces 28 of the back side panels 134 are adapted to refastenably connect the waist regions together. This allows the product to have fewer components, which makes the product more underwear-like and provides manufacturing efficiencies. Accordingly, the attachment panels 134 can consist of, or can consist essentially of, an elastomeric nonwoven material, rather than incorporating separate patches, strips or tabs of fastening component material to engage the first and second fastening components 84 and 85. Desirably, the sole means for refastenably connecting the first and second waist regions in a pant configuration can consist of the mechanical fastening elements 84 and 85 in the front waist region and the inner attachment surfaces 28 of the attachment panels 134. Also, this product configuration allows the first and second fastening components 84 and 85 to be located on the outer surface 30 facing away from the wearer, thereby reducing the likelihood of irritating the skin of the wearer.

The training pant 20 may further include releasable side bonds (not shown) for improved reliability of maintaining the pant in a prefastened condition particularly when it is being pulled on or off over the hips of the wearer. Such releasable side bonds are desirably configured to be readily broken such that the caregiver can easily remove the training pant 20 after it has been soiled. The releasable side bonds desirably comprise ultrasonic point bonds. Absorbent articles including such releasable side bonds are further described in U.S. patent application Ser. No. 09/100,574 titled "Disposable Absorbent Articles Having Passive Side Bonds And Adjustable Fastening Systems" filed Jun. 19, 1998 by Elsberg, which is incorporated herein by reference.

Figure 9:
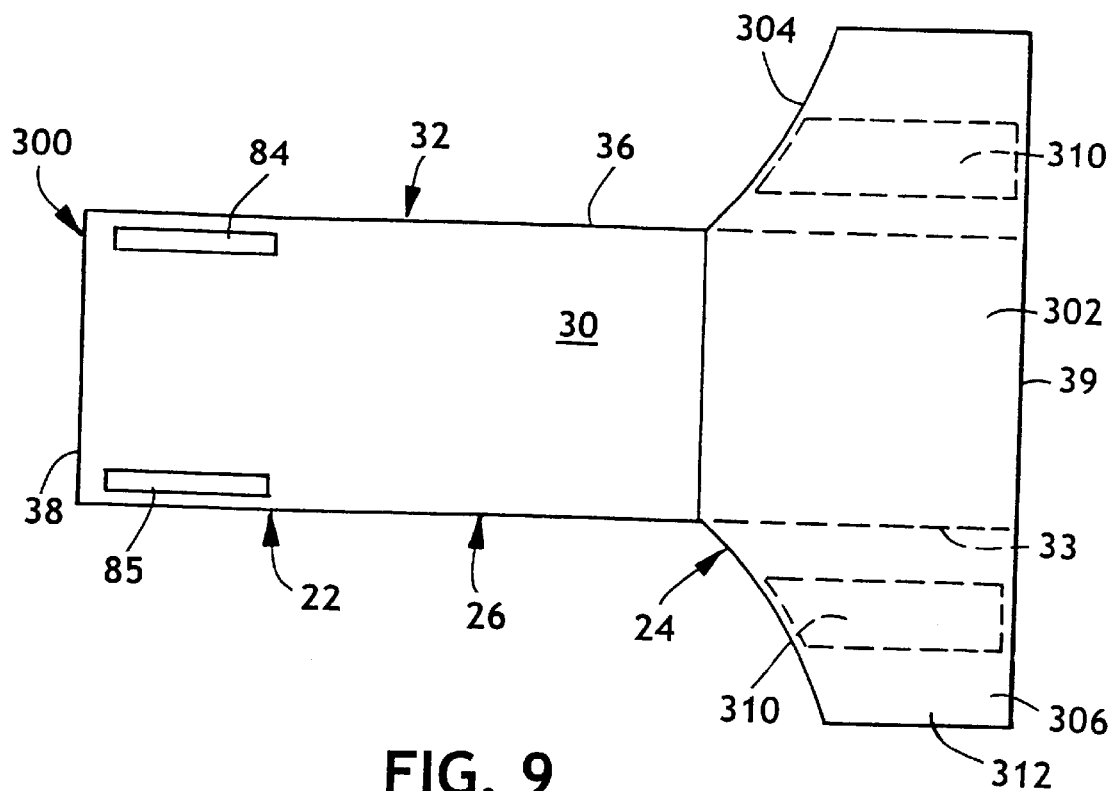
FIG. 9 illustrates a plan view of an alternative disposable absorbent article shown in an unfastened, stretched and laid flat condition, and showing the surface of the article that faces away from the wearer.

An alternative training pant 300 is illustrated in a stretched and laid flat condition in FIG. 9. The training pant 300 includes first and second fastening components 84 and 85 disposed in the front waist region 22 on the outer surface 30. The training pant 300 also includes a panel member 302 disposed in the back waist region 24. The panel member 302 desirably forms first and second attachment panels 304 and 306 that extend transversely outward from the composite structure 33 and the absorbent assembly 44 (FIG. 3) in the back waist region 24. The panel member 302 can comprise an integral portion of a component of the composite structure 33, such as the bodyside liner 42 or a layer of the outer cover 40; or comprise a separate element bonded to the composite structure; or comprise a plurality of layers, whether integral portions, separate elements, or a combination thereof.

Figure 10:
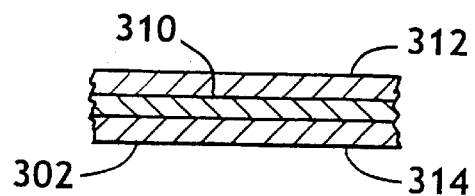
FIG. 10 illustrates an enlarged sectional view of a portion of an attachment panel of the absorbent article shown in FIG. 9.

The panel member 302 and thus the attachment panels 304 and 306 can comprise either an elastic material or an inelastic material. With additional reference to FIG. 10, the panel member 302 in the illustrated embodiment comprises a plurality of elastomeric segments 310 disposed between an outer facing layer 312 and an inner facing layer 314. The inner facing layer 314 of the attachment panels 304 and 305 thus provides an inner attachment surface that is adapted to refastenably engage the fastening components 84 and 95.

The elastomeric segments 310 can be positioned and arranged so that both attachment panels 304 and 305 have elastic properties in a direction parallel to the transverse axis 49 of the training pant 300. The elastomeric segments 310 can comprise elastomeric films, webs, strands, fibers or the like, and can comprise elastic materials similar to those described in relation to other elastic components of the training pants 20 and 300. The facing layers 312 and 314 can comprise materials of the type described in relation to the bodyside liner 42, the side panels 34 and 134, or the like.

Figure 4:
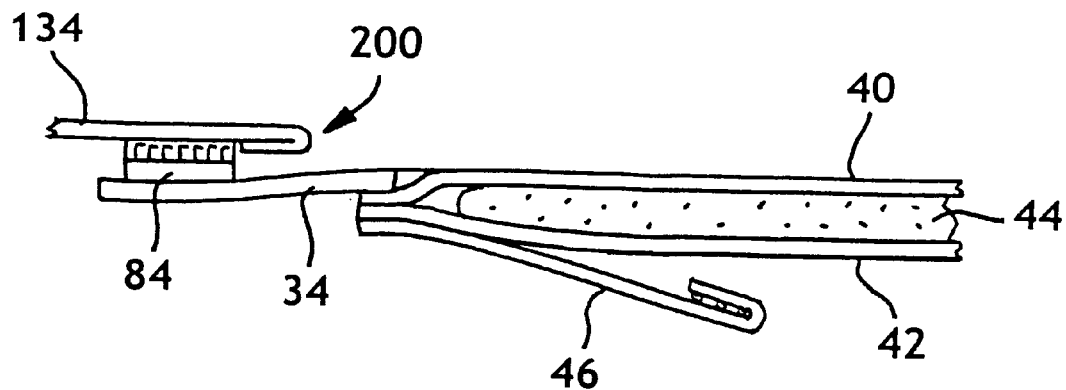
FIG. 4 illustrates a sectional view of the back side panel releasably engaged with a fastening component according to one embodiment of the invention.

FIG. 4 illustrates a sectional view of an attachment panel 134 (or 304) releasably engaged with a fastening component 84. The attachment panel 134 can include a hem 200 at the distal edge 68. The hem 200 consists of a folded portion of the attachment panel material and bonded to itself by adhesive, sonic bonds, thermal bonds or other suitable means known in the art. The hem 200 can either be used as a finger tab or a reinforced area for engagement with the fastening component 84. When used as a finger tab, the hem 200 also functions as a stop to limit creep of the fastening component 84 relative to attachment panel 134.

Figure 5:
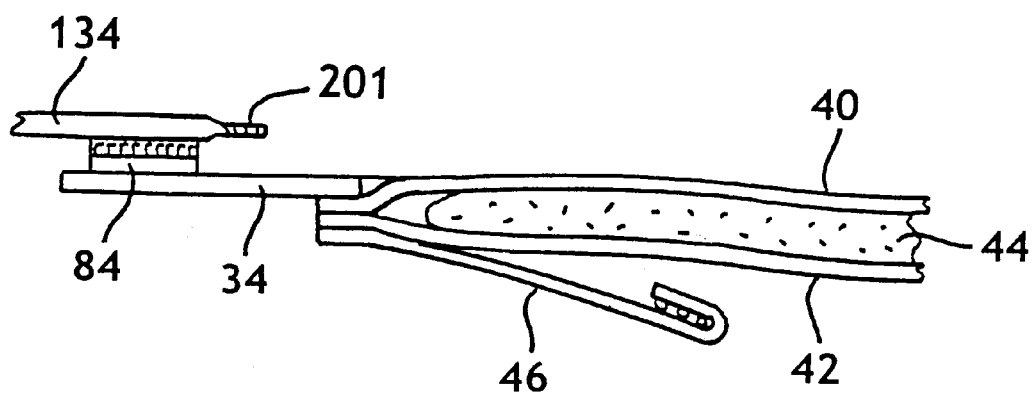
FIG. 5 is similar to FIG. 4 but illustrating an alternative embodiment of the invention.

FIG. 5 illustrates a refastenable seam location indicator 201 formed at the distal edge 68 of the attachment panel 134 (or 304). The indicator 201 is formed by embossing or bonding the layers of the attachment panel material using mechanical, sonic or thermal means. The indicator may include a message or design.

Figure 6:
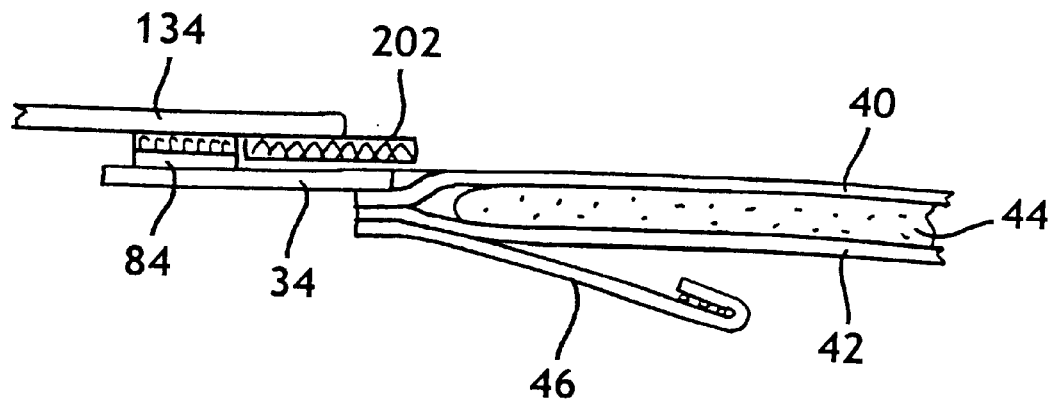
FIG. 6 is similar to FIG. 4 but illustrating another alternative embodiment of the invention.

The attachment panel 134 (or 304) shown in FIG. 6 includes a refastenable seam location indicator 202 that also functions as a stop similar to the hem 200 in FIG. 4. The indicator 202 comprises a separate strip of material bonded to the attachment panel 134. In particular embodiments, the indicator 202 comprises nonelastic nonwoven material, and is desirably less engageable than the attachment panel, or not engageable, with the fastening component 84.

Figure 7:
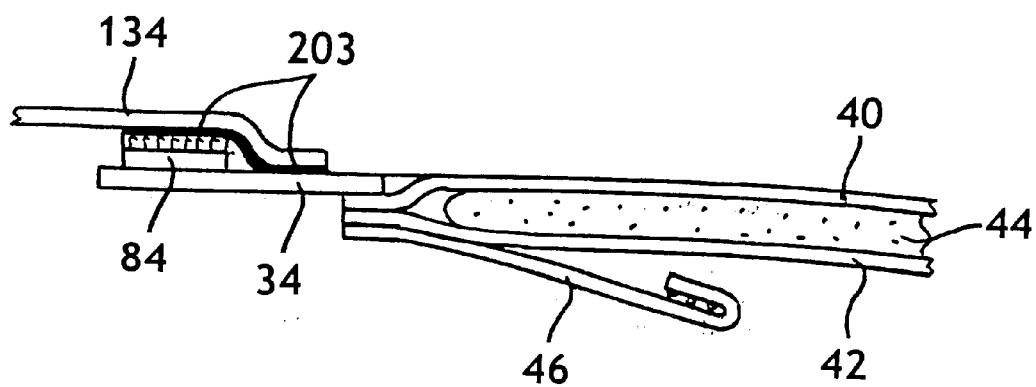
FIG. 7 is similar to FIG. 4 but illustrating a further alternative embodiment of the invention.

In FIG. 7, the attachment panel 134 (or 304) includes an adhesive coating 203 disposed on the inner surface. The adhesive coating 203 is adapted to engage the fastening component 84 and the outer cover 40 to hold the overlap of the attachment panel 134 onto the outer cover 40. The adhesive maintains its tack so that it can be repeatedly engaged and disengaged. Adhesives suitable for forming such a coating are described generally as construction adhesives, and are available from various adhesive suppliers such as National Starch, Bridgewater, N.J., U.S.A. In one particular embodiment, the adhesive comprises an SBS block copolymer having a modulus of about $10^9$ to $10^{10}$ and a shear rate of 10 radians/sec, an example of which is identified as National Starch No. 345610 or 5610. The adhesive may be applied at an add-on level of about 1 gram per square meter or less, such as about 0.4 to about 0.6 grams per square meter. In this way the fit and appearance of the training pant 20 more closely resembles a garment.

Figure 11:
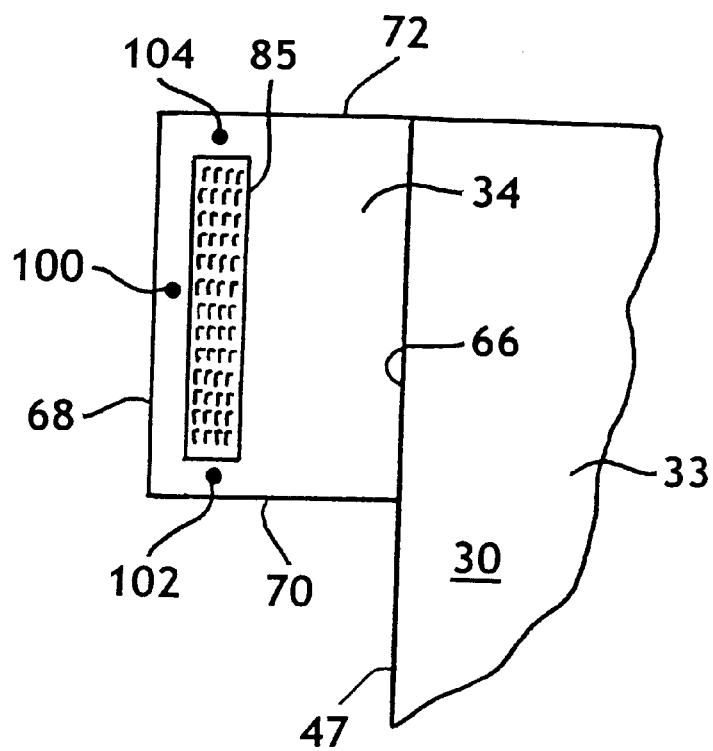
FIG. 11 illustrates an enlarged plan view of a front side panel of the type shown in FIG. 2.

An enlarged plan view of a front side panel 34 of the type shown in FIG. 2 is illustrated in FIG. 11. Only one side panel 34 is shown in FIG. 11, although it should be understood that other side panels can employ a similar construction. The side panel 34 can be bonded to and extend transversely beyond the linear side edge 47 of the composite structure 33 along attachment line 66. The side panel 34 defines a distal edge 68 that is spaced from the attachment line 66, a leg end edge 70 disposed toward the longitudinal center of the training pant 20, and a waist end edge 72 disposed toward a longitudinal end of the training pant.

In particular embodiments, the fastening component 85 is spaced inward from the distal edge 68 and the end edges 70 and 72 in order to protect the wearer from irritation that might be caused by contact with the fastening component. Specifically, the fastening component 85 can be spaced transversely inward from the distal edge 68 in the region of reference numeral 100. Also, the fastening component 85 can be spaced longitudinally inward from the leg end edge 70 in the region of reference numeral 102, and spaced longitudinally inward from the waist end edge 72 in the region of reference numeral 104.

The degree of spacing balances the fact that a smaller distance is harder for children and parents to remove but provides a more garment-like appearance, while a larger distance is easier for children and parents to remove but provides a loose and floppy appearance that is not garment-like. Thus, the fastening component 85 is desirably spaced transversely inward from the distal edge 68 by about 1 to about 15 millimeters, particularly about 1 to about 5 millimeters, such as about 2 millimeters. The fastening component 85 is desirably spaced longitudinally inward from the leg end edge 70 and from the waist end edge 72 by about 2 millimeters or more, particularly about 5 millimeters or more, such as from about 5 to about 15 millimeters.

Figure 12:
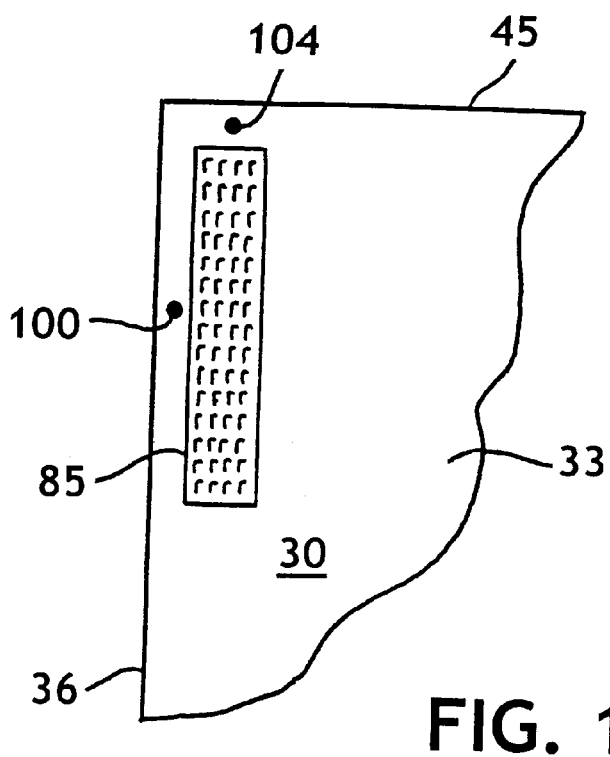
FIG. 12 illustrates an enlarged plan view of a front side panel of the type shown in FIG. 9.

FIG. 12 illustrates an enlarged plan view of a front side panel of the type shown in FIG. 9. As with the embodiment illustrated in FIG. 11, the fastening component 85 can be spaced transversely inward from the side edge 36 in the region of reference numeral 100 and longitudinally spaced inward from the end edge 45 in the region of reference numeral 104. The preferred distances from the edges are the same as those specified above in relation to the embodiment of FIG. 11.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. An absorbent article defining a longitudinal axis, an overall length dimension measured parallel to the longitudinal axis, a transverse axis, first and second longitudinally spaced waist regions, a crotch region which extends between and interconnects the first and second waist regions, an inner surface and an opposite outer surface, the absorbent article adapted to provide a pant configuration having a waist opening and a pair of leg openings, the absorbent article comprising:

an absorbent chassis comprising an absorbent assembly;

attachment panels extending transversely outward from the absorbent assembly in the first waist region, the attachment panels having a length dimension that is about 20 percent or greater of the overall length dimension, each attachment panel comprising a nonwoven substrate that extends from the waist opening to one of the leg openings and defines an inner attachment surface; and at least one fastening component disposed in the second waist region on the outer surface, the at least one fastening component comprising a mechanical fastening element adapted to refastenably engage the inner attachment surfaces;

wherein the refastenable engagement of the mechanical fastening element and the inner attachment surfaces maintains the absorbent article in the pant configuration;

wherein the sole means for refastenably connecting the first and second waist regions in the pant configuration consists of the inner attachment surfaces in the first waist region and the mechanical fastening elements in the second waist region.

2. An absorbent article defining a longitudinal axis, a transverse axis, front and back longitudinally spaced waist regions, a crotch region which extends between and interconnects the front and back waist regions, an inner surface and an opposite outer surface, the absorbent article adapted to provide a pant configuration having a waist opening and a pair of leg openings, the absorbent article comprising:

an absorbent chassis comprising a liquid permeable bodyside liner, a liquid impermeable outer cover bonded to the bodyside liner, and an absorbent assembly disposed between the bodyside liner and the outer cover;

first and second attachment panels bonded to the absorbent chassis in the back waist region and extending transversely outward from the absorbent chassis, the first and second attachment panels comprising an elastomeric nonwoven material and having inner attachment surfaces; and at least one fastening component disposed in the front waist region on the outer surface, the at least one fastening component comprising a plurality of engaging elements projecting outward from the outer surface and adapted to refastenably engage the inner attachment surfaces of the attachment panels;

wherein the refastenable engagement of the attachment panels to the at least one fastening component maintains the absorbent article in the pant configuration, wherein the sole means for refastenably connecting the front and back waist regions in the pant configuration consists of the elastomeric nonwoven material in the back waist region and the plurality of engaging elements in the front waist region.

3. An absorbent article defining a longitudinal axis, a transverse axis, front and back longitudinally spaced waist regions, a crotch region which extends between and interconnects the front and back waist regions, an inner surface and an opposite outer surface, the absorbent article adapted to provide a pant configuration having a waist opening and a pair of leg openings, the absorbent article comprising:

an absorbent chassis comprising a liquid permeable bodyside liner, a liquid impermeable outer cover bonded to the bodyside liner, and an absorbent assembly disposed between the bodyside liner and the outer cover;

first and second attachment panels extending transversely outward from the absorbent chassis in the back waist region, the first and second attachment panels comprising an elastomeric nonwoven material and having inner attachment surfaces; and at least one fastening component disposed in the front waist region on the outer surface, the at least one fastening component comprising a plurality of engaging elements projecting outward from the outer surface and adapted to refastenably engage the attachment surfaces of the attachment panels;

wherein the refastenable engagement of the attachment panels to the at least one fastening component maintains the absorbent article in the pant configuration, wherein the sole means for refastenably connecting the front and back waist regions in the pant configuration consists of the elastomeric nonwoven material in the back waist region and the plurality of engaging elements in the front waist region.

* * * * *